United States Patent [19]

Mobin-Uddin

[11] Patent Number: 4,643,184

[45] Date of Patent: Feb. 17, 1987

[54] EMBOLUS TRAP

[76] Inventor: Kazi Mobin-Uddin, 393 E. Town St., Suite 115, Columbus, Ohio 43215

[21] Appl. No.: 601,220

[22] Filed: Apr. 17, 1984

Related U.S. Application Data

[63] Continuation-in-part of Ser. No. 428,254, Sep. 29, 1982, abandoned.

[51] Int. Cl.$^4$ .............................................. A61B 17/00
[52] U.S. Cl. .................................. 128/303 R; 128/345
[58] Field of Search .................... 128/130, 1 R, 303 R, 128/345, 325, 344, 341, 343, 328; 604/104, 105, 604/106

[56] References Cited

U.S. PATENT DOCUMENTS

| | | | |
|---|---|---|---|
| 3,334,629 | 8/1967 | Cohn | 128/325 |
| 3,540,431 | 11/1970 | Mobin-Uddin | 128/1 R |
| 3,952,747 | 4/1976 | Kimmell | 128/303 R |
| 4,425,908 | 1/1984 | Simon | 128/345 X |

FOREIGN PATENT DOCUMENTS 12349  5/1896  Switzerland ........................ 604/106

Primary Examiner—Michael H. Thaler
Attorney, Agent, or Firm—Buell, Ziesenheim, Beck & Alstadt

[57] ABSTRACT

The device comprises a plurality of elongated filamentary loops extending outwardly from a central column in one or more tiers, the filaments having hooks backed by offset barriers at their free ends. The column is preferably hollow. The device is inserted into a passageway such as a vein with the loops held back toward the column and biased to open when released, and hook into the vein wall to form a network or web to engage and hold blood clots in the vein. The device anchors itself in place without injury to the wall of the passageway. It is self-centering and self-cleaning. Preferably the device is inserted over a wire guide threaded through the column and introduced into the vein through a hollow needle puncture.

14 Claims, 23 Drawing Figures

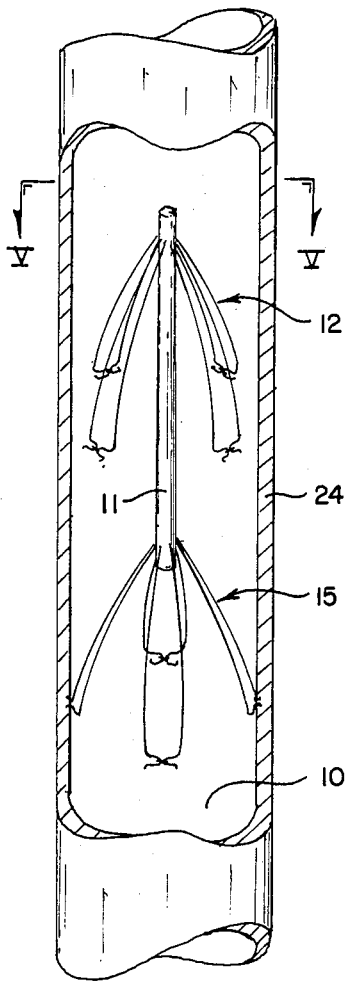
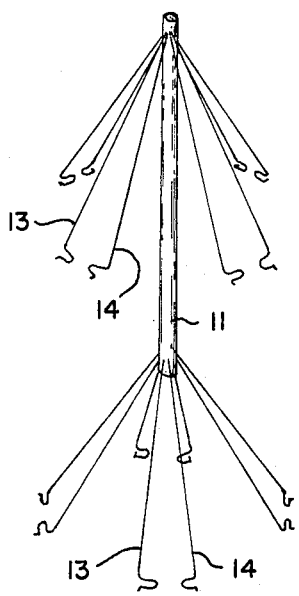
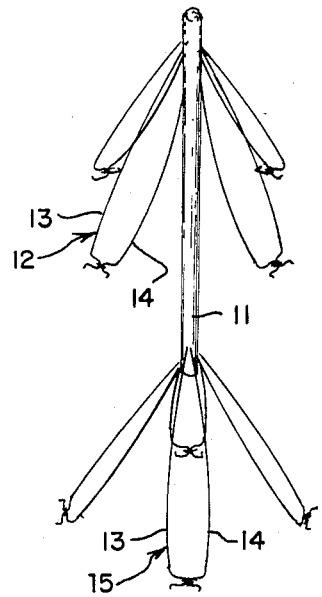
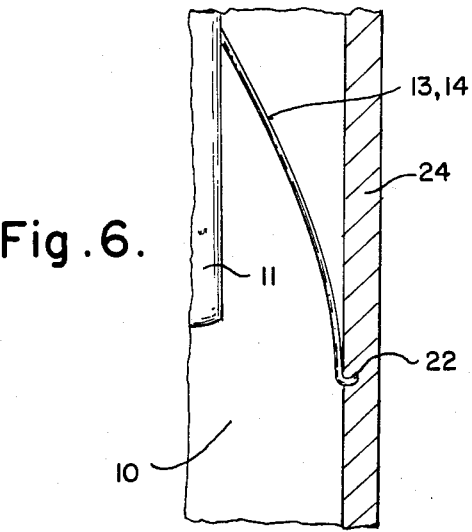
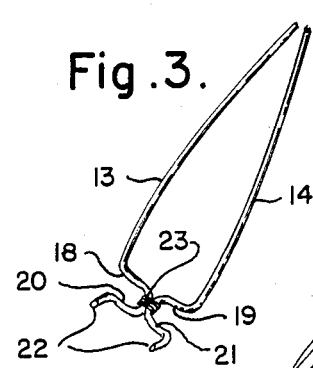
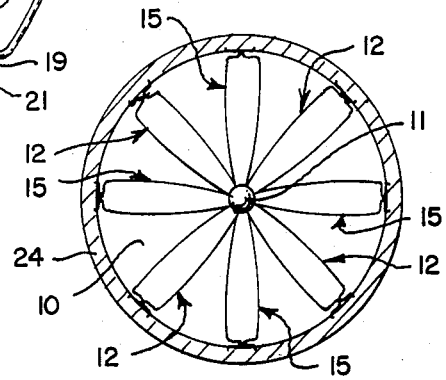

The vein is entered with a needle puncture.

Wire guide is passed through the needle into the vein.

The needle is removed. Wire guide remains in place.

The introducer and sheath are advanced over the wire guide into the vein.

The wire guide and introducer are removed leaving the sheath in place.

EMBOLUS TRAP

This application is a continuation-in-part of my co-pending application Ser. No. 428,254, filed Sept. 29, 1982, now abandoned captioned Blood Clot Engaging Device for Fluid Passageways.

FIELD OF THE INVENTION

This invention relates to a device for implanting in a fluid passageway of the human body, preferably in the inferior vena cava, and to a method of implanting it. My embolus trap traps migrating blood clots traveling upstream in human veins and prevents them from reaching the lungs. My invention is more particularly concerned with an embolus trap which may be implanted either through the jugular vein, subclavian vein or through the femoral vein, and with specific procedures for such implanting.

BACKGROUND OF THE INVENTION

The problem addressed by my invention arises especially with persons who have had operations. The extended time in which such a person must lie supine in bed not infrequently leads to the development of blood clots which are carried by the veins to the heart, and by reason of the structure of the human body through the inferior vena cava. As these clots enter the heart at least some are pumped outwardly through the artery which leads to the lungs. It is here that by reason of the numerous small passageways which characterize the lungs that the clots block certain of the blood passageways. This may lead to sudden death because here the clots act so that the blood flow to the lungs is interrupted or obstructed and the rejuvenation required by the oxygenation process cannot take place.

In the past, this problem has been met by a major surgical operation which requires a tying of the inferior vena cava and the collateral circulation which results is relied upon to provide passageways for the transmittal of satisfactory blood flow to the heart. Because this surgical operation of tying the vena cava is usually performed on a person who has already been weakened by other surgery, and by reason of the fact that it requires a rather extensive incision through the trunk area to reach the vena cava to tie it, it is considered a major and generally dangerous operation.

Anticoagulation agents are effective in many cases; nevertheless formation of blood clots in the veins of the lower extremities and migration thereof to lungs continues to be a major health hazard, especially in hospitalization, resulting in morbidity and mortality.

Mechanical devices have been developed for insertion into the vena cava by a simple catheter technique under local anesthetic, thus avoiding a major operation under general anesthesia. One such device is disclosed in Mobin-Uddin U.S. Pat. No. 3,540,431 of Nov. 17, 1970. This device is of umbrella-type configuration including skeletal framework and a hood of filtering media for lodgement in spanning relation of a vein or passageway of the human body to filter fluid flowing in a closed passageway. The undesirable features of this device are: (1) dislodgement and migration in a small percentage of patients; and (2) tendency to clogging up resulting in the development of collateral circulation. Another such device is disclosed in Kimmell U.S. Pat. No. 3,952,747 of Apr. 27, 1976. It comprises a plurality of convergent legs in generally conical array and joined at their convergent ends to an apical hub, each leg having a reversely bent hook at its end which is distal with respect to the hub. Each leg also includes a plurality of bends intermediate its length, which bends decrease the solids by-pass capability of the filter without concurrent fluid occlusion.

It has been found that such devices migrate through the blood vessel or passageway resulting in a potentially dangerous complication of internal bleeding and perforation of adjacent important organs. Also this device at times when ejected from the catheter into the vein positions itself sideways or tilted inside the passageway, with resulting increased tendency to an undesirable penetration through the vein wall.

THE INVENTOR'S SOLUTION TO THE PROBLEM

The embolus trap of my invention is an expansible article which is inserted in its collapsed condition in a passageway and which then opens and anchors itself. It comprises a central hollow column carrying preferably two or more tiers spaced therealong of radially extending elongated filaments, pairs of which are connected at their outer ends to form loops. Each tier includes two or more such loops and the loops of one tier are positioned circumferentially between the loops of the next adjoining tier. At the outside ends the filaments are formed into outwardly extending hooks backed by offsets, the latter limiting the penetration of the hooks into the wall of a passageway in which my device is implanted. The filaments are preferably made of metal wire or other filament with sufficient spring to permit them to be folded back against the central column while my device is inserted into a passageway and then when released to assume a radially extended position within the passageway forcing their hooked ends against the passage wall.

My device above described is inserted into a vein by a catheter of plastic tubing having a tubular capsule at its distal end containing my device in its collapsed condition. A wire guide extends through the hollow central column of my device and out beyond the capsule. The wire guide has a flexible J-tip at its outer end which facilitates maneuvering and prevents anchoring in the wall of the vein. A hollow push rod which fits over the wire allows the catheter to eject my embolus trap from the capsule so that it travels along the wire guide to its destination. For maneuvering the capsule in place a different type of hollow rod is provided which will not eject the embolus trap from the capsule.

BRIEF DESCRIPTION OF THE DRAWINGS

FIG. 1 is an isometric view of an embodiment of my embolus trap in an intermediate stage of manufacture;

FIG. 2 is an isometric view of the completed article of FIG. 1;

FIG. 3 is an enlarged detail of the hooks and offsets of a loop of FIG. 2;

FIG. 4 is an isometric view of the article of FIG. 2 in an open position in a vein or like passageway;

FIG. 5 is a section taken on the plane V—V of FIG. 4;

FIG. 6 is an enlarged detail showing hook engagement with a wall of a vein or like passageway;

DESCRIPTION OF PREFERRED EMBODIMENT

Figure 7:
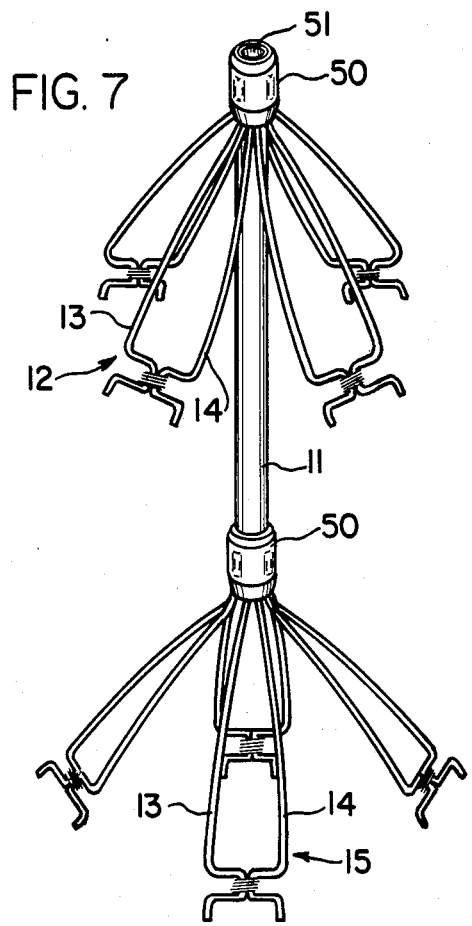
FIG. 7 is an isometric view of an embodiment of my embolus trap shown in FIG. 2 presently preferred by me.

My embolus trap comprises a central cylindrical column 11 to which is attached a plurality of upper elongated loops 12 of filaments 13 and 14, such as metal wire, and a plurality of like lower loops 15. Loops 12 and 15 are assembled in two tiers spaced from one another on column 11, as are shown in FIGS. 1, 2, 4, 5 and 7. The loops 12 in the upper tier are circumferentially spaced from each other in symmetrical fashion, as are the loops 15 in the lower tier. The loops of adjacent tiers are displaced from each other circumferentially, preferably centrally, so that a loop 12 of the upper tier is centrally located between two loops 15 of the lower tier, and vice versa. The loops as shown in FIGS. 4, 5 and 6 are in their extended position within a passageway 10, each inclined outwardly from column 11 and making contact at its outer end with the wall 24 of passageway 10. Each of loops 12 and 15 is formed of two wires 13 and 14. The inner ends of adjoining filaments, such as 13 and 14, are anchored in central column 11 and the outer ends of those filaments are joined or abutted to form a closed elongated loop as is shown in FIG. 3. The outer ends of filaments 13 and 14 are bent toward each other to form short circumferentially extending portions 18 and 19 respectively, and then 180° in the same plane to form oppositely extending circumferential portions 20 and 21 respectively, as is shown in FIG. 3. The extreme ends of portions 20 and 21 are bent radially outwardly into hooks 22 as is also shown in FIG. 3. The wires of each loop may be joined at the crowns of the open loops formed by bent portions 18 and 20 of wire 13 and 19 and 21 of wire 14, as by tying the wires over the loops with 7-0 polypropylene suture 23. Those circumferentially bent portions 20 and 21 form a stop or barrier which prevents hooks 22 from penetrating the wall 24 of the passageway 10 sufficient to puncture it.

While the various filaments 13 and 14 may be attached to central column 11 in any convenient manner, I prefer the structure shown in FIG. 7. The filaments in each tier are positioned in pairs at the desired spacing around column 11, enclosed in a metal sleeve 50, and are welded thereto at an end of the sleeve. The sleeve 50 with filaments attached is then crimped on column 11. Column 11 is hollow, and preferably rigid, having a central cavity 51 running therethrough.

Although I have described and illustrated four-loop tiers, a two or more tier embodiment may have only two loops per tier, providing that they are rotated with respect to each other sufficiently to effect proper centering. Tiers of three loops or more may be used if desired. Several loops in a single tier may be used. The loops of a tier are preferably shaped so that the areas between the loops are slightly greater than the areas within the loops, and successive tiers are disposed so that a loop of one tier is axially spaced from a space between loops of an adjoining tier.

While I have described a central column with protruding wires or filaments formed into loops, the disposition of wire struts attached to the central column can be varied to achieve any desired shape or configuration. The wire struts may be arranged in a plurality of angularly disposed pairs, longitudinally spaced and rotatively displaced around the axis of the central column.

When my device is implanted in a vein, for example, as above described, the loops form a central network or web extending over the entire cross section of the vein. A similar network or web is likewise formed by each additional spaced tier of my device. The several tiers are kept in alignment by the central column, thus insuring that each above mentioned web or network is normal to the vein axis. A blood clot approaching my device and being engaged in a loop or loops tends to slide along the wires toward the center impelled by the motion of the bloodstream and to become wedged between the loop and the column. It is thus held in a place where the flow of the bloodstream around it tends to lyse or dissolve the clot.

The hooks, as have been mentioned, penetrate the vein wall a controlled amount, so anchoring the device. They are caused to do so by the outward springing of the loops when my device is released from its capsule in a vein. The angle of the hook is canted or adjusted to maximize its holding effect and the dimensions of the hook are adjusted to prevent perforation of the vein wall. The barrier behind each hook formed by the offset bends in the wire previously described effectively limits hook penetration of the vein wall to a safe amount and eliminates any tendency of the hooks to work themselves through the vein wall.

It will be evident from the above description that my clot engaging device adjusts itself to veins or other passageways of a considerable range of sizes and is self-centering. Because its hooks are canted so as to be urged toward the vein wall by the flow of blood in a vein it will not dislodge and migrate either upstream or downstream.

Figure 8:
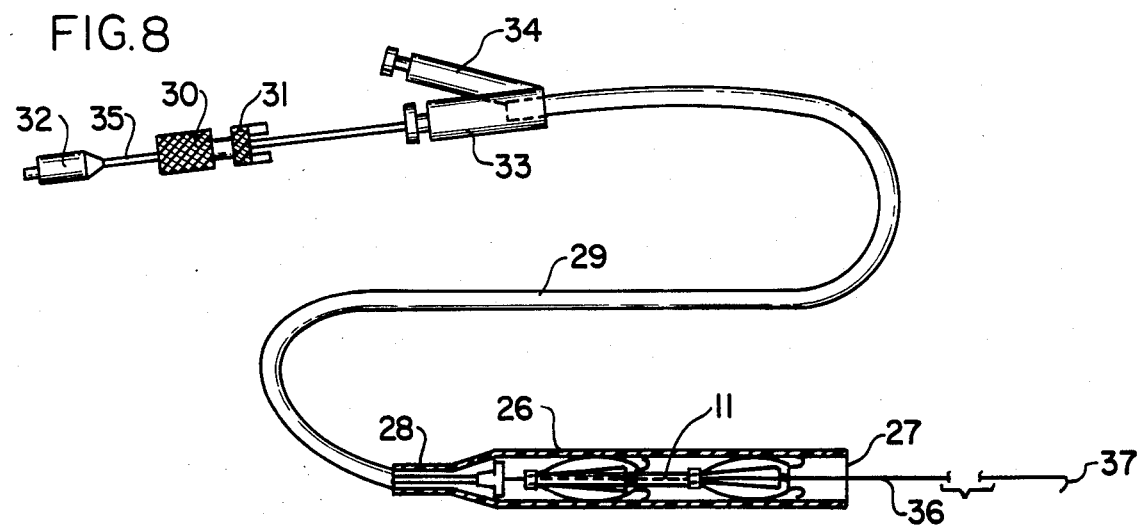
FIG. 8 is an assembly of my embolus trap in its catheter.

The apparatus for inserting my embolus trap of FIG. 7 in a vein is shown in FIG. 8. A catheter assembly suitable for my purpose is likewise shown in that figure. A tubular capsule 26 of smaller diameter than a jugular vein has an open end 27 and an opposite end 28 of reduced diameter which is connected through plastic flexible tubing 29 with a terminal sleeve 30. Sleeve 30 may be provided with a locking device 31 which compresses tube 29 against an operating rod therein. That operating rod or wire 35 extends axially through sleeve 30 into an operating knob 32 and its other end into capsule 26. Tube 29 may pass through a fitting 33 which has a sideport 34 for injection purposes. Knob 32 may have a fitting for center injection.

Figure 12:
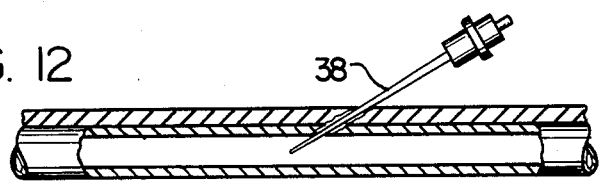
FIGS. 12 through 16 illustrate certain stages in my process.
Figure 13:
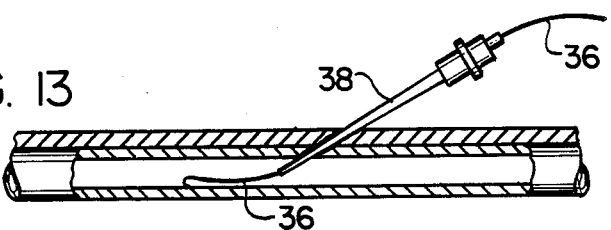
Figure 14:
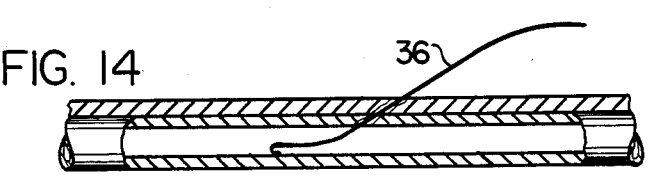
Figure 15:
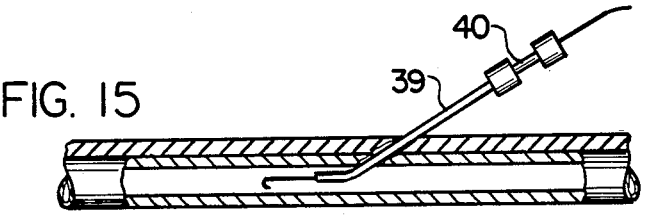
Figure 16:
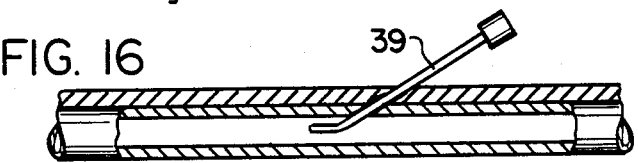

Operating rod 35 is removable and may take several forms as may be required at different stages of my method of operation. In order to make clear the functions of my apparatus it will be necessary to describe its method of use. The various steps of placement of an introducer sheath for my embolus trap are shown in FIGS. 12-16 inclusive. FIG. 12 shows puncture of a vein by a hollow needle 38. In FIG. 13 a wire guide 36, also shown in FIG. 8, is passed through hollow needle 38 into the vein. In FIG. 14 hollow needle 38 is removed over wire guide 36 leaving the latter in place. In FIG. 15 an introducer sheath 39 and introducer 40 are slipped over wire guide 36 and into the vein. In FIG. 16 the wire guide 36 and introducer 40 are removed leaving introducer sheath 39 in the vein.

Figure 9:
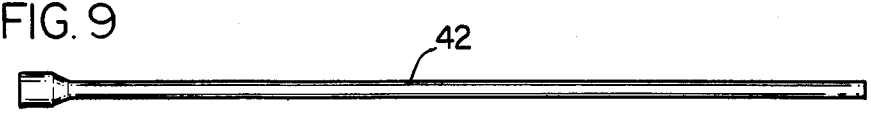
FIGS. 9, 10 and 11 illustrate certain accessories used with my catheter.
Figure 10:

Wire guide 36 above described is used only to lead the sheath 39 into place. It is not intended to reach the site where the embolus trap is to be stationed. It has a flexible J-tip 37 at its free end to prevent anchoring. After it is removed, my embolus trap is collapsed and loaded into capsule 26 and a second wire guide 36 similar to the first but appreciably longer is threaded through the central hole 51 in column 11 of my trap. The long wire guide 36 is then introduced into the vein through sheath 39 until its J-tipped end 37 reaches the desired location in the vein. The capsule 26 is then advanced over wire guide 36 into the vein to the desired location and wire guide 36 is withdrawn. A hollow push rod 42 shown in FIG. 9 is then introduced through tubing 29 and pushes my embolus trap out of capsule 26 into the vein. The catheter is then removed. If it is necessary to work or maneuver my embolus trap into its proper place, hollow tube maneuvering rod 43 shown in FIG. 10 may be slipped over wire guide 36. The distal end of rod 43 is bent so that when that end is inserted into capsule 26 it does not engage the embolus trap. Thus, it can be used to maneuver capsule 26 without danger of ejecting the embolus trap.

Figure 11:
Figure 17:
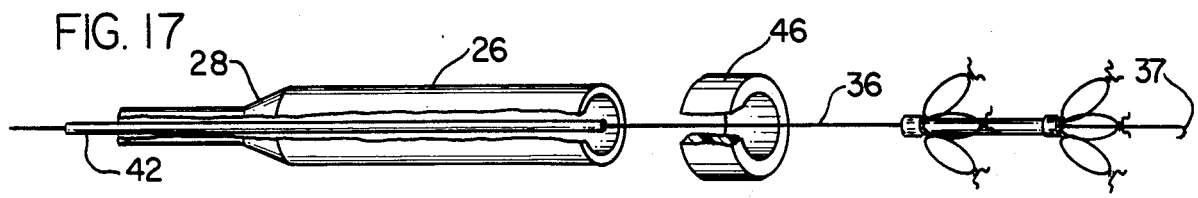
FIGS. 17, 18 and 19 illustrate the stages of loading my embolus trap into the capsule of my catheter for jugular/subclavian implant.
Figure 18:
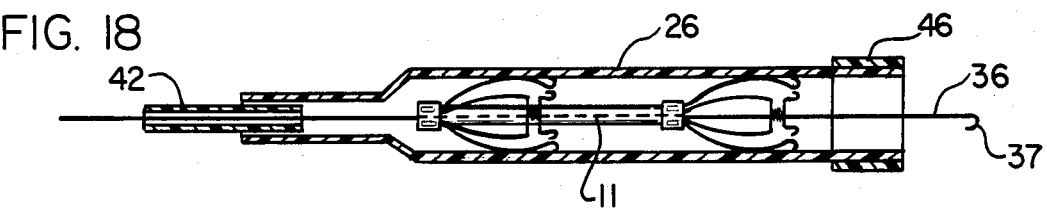
Figure 19:
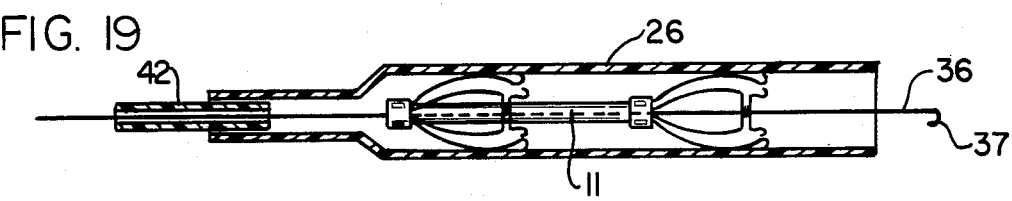
Figure 20:
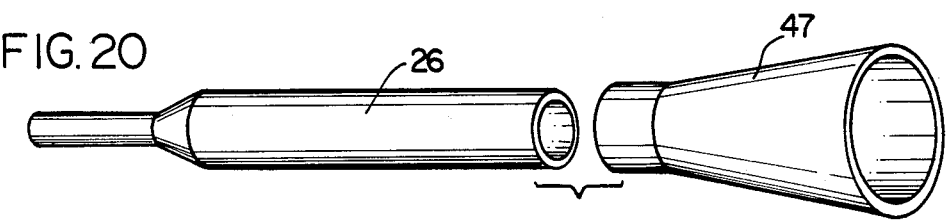
FIGS. 20 through 23 illustrate the stages of loading my embolus trap into the capsule of my catheter for femoral implant.
Figure 21:
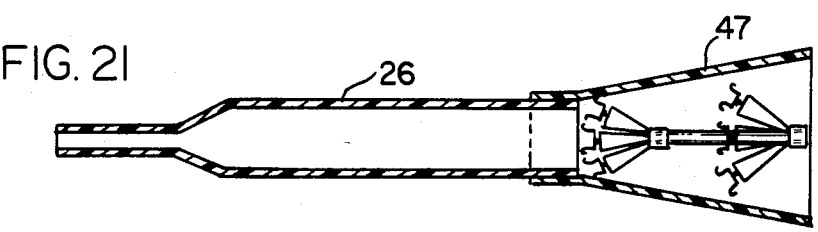

The process of loading my embolus trap into the capsule of the catheter is somewhat different for jugular subclavian approach than it is for femoral approach, as the embolus trap is loaded in reverse direction. FIGS. 17, 18 and 19 illustrate the procedure for jugular implants. Hollow push rod 42 is introduced into capsule 26 and wire guide 36 is threaded through it and out the open end of capsule 26. That wire guide is also passed through a loading sleeve or cone 46 which fits over the open end of capsule 26 and through hollow column 11 of my embolus trap from top to bottom, as that trap appears in FIG. 7. Then with the help of pin 44 shown in FIG. 11, the embolus trap is pushed through loading cone 46 which collapses its filaments against its center column and into capsule 26, while hollow push rod 42 is withdrawn through capsule end 28. The embolus trap in place in capsule 26 is shown in FIG. 19.

Figure 22:
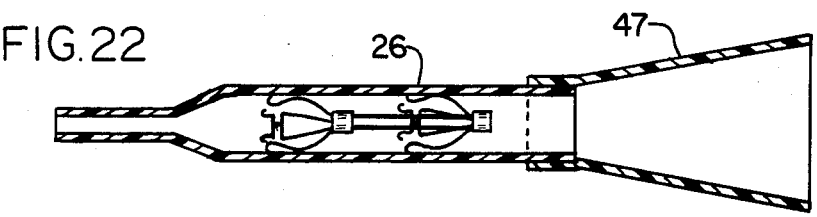
Figure 23:
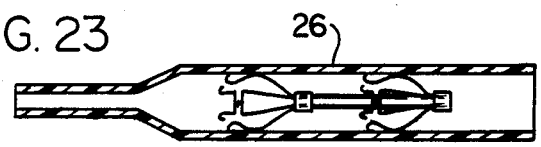

The process of loading my embolus trap into capsule 26 for femoral implanting is shown in FIGS. 20 through 23. No wire guide or hollow push rod is required. Loading cone 47 is fitted onto the open end of capsule 26. My embolus trap is introduced into the cone in FIG. 21, bottom end first, as it is positioned in FIG. 7. The tapering cone collapses the wire filaments and with the help of pin 44 the trap is pushed into capsule 26, as is shown in FIG. 22. Then the loading cone 47 is removed. My embolus trap in place in capsule 26 is shown in FIG. 23.

While I have shown and described a present preferred embodiment of my invention and I have illustrated a present preferred method of practicing the same, it is to be distinctly understood that the invention is not limited thereto but may be otherwise variously embodied within the scope of the following claims.

I claim:

1. An embolus trap for positioning in spaced relation in a fluid passageway in the human body comprising a tubular central column and one or more axially spaced tiers of radially outwardly urged elongated loops of filaments spaced around the column inclined thereto and attached thereto at one end, the other ends of at least some of the filaments terminating in at least one hook backed by a circumferential offset limiting the penetration of the hook into the wall of the fluid passage.

2. Apparatus of claim 1 in which the central column is made of rigid material.

3. Apparatus of claim 1 in which the hooks and the offsets are integral portions of the filaments.

4. Apparatus of claim 1 in which the filaments are metal wire.

5. Apparatus of claim 4 in which the outer end of a loop comprises two lengths of wire each bent away from the other circumferentially to form an offset and then outwardly to form hooks.

6. Apparatus of claim 5 in which the two lengths of wire are bent toward each other and then away from each other to form the offset.

7. Apparatus of claim 5 or 6 in which the two lengths of wire are joined at their outer ends adjacent their hooks.

8. Apparatus of claim 7 in which the lengths of wire are joined at their outer ends by a fiber strand tied therearound.

9. Apparatus of claim 1 in which all loops have substantially the same area.

10. Apparatus of claim 1 in which the open area between adjoining loops is somewhat greater in extent than the area of a loop.

11. Apparatus of claim 1 in which the number of tiers is at least two.

12. Apparatus of claim 11 in which the loops of each tier are circumferentially displaced from the loops of the next adjoining tier.

13. Apparatus of claim 11 in which each tier has the same number of loops and the same spacing between loops.

14. Apparatus of claim 1 in which the filaments are attached to the central column by a metal sleeve surrounding them and affixed to them at their attached ends and crimped against the central column.

* * * * *